US010302599B2

(12) United States Patent
Tumpold et al.

(10) Patent No.: US 10,302,599 B2
(45) Date of Patent: May 28, 2019

(54) PHOTOACOUSTIC GAS DETECTOR

(71) Applicant: Infineon Technologies AG, Neubiberg (DE)

(72) Inventors: David Tumpold, Kirchheim (DE); Alfons Dehe, Reutlingen (DE); Christoph Glacer, Munich (DE)

(73) Assignee: Infineon Technologies AG, Neubiberg (DE)

( * ) Notice: Subject to any disclaimer, the term of this patent is extended or adjusted under 35 U.S.C. 154(b) by 211 days.

(21) Appl. No.: 15/335,511

(22) Filed: Oct. 27, 2016

(65) Prior Publication Data

US 2018/0120266 A1 May 3, 2018

(51) Int. Cl.
*G01N 29/24* (2006.01)
*G01N 29/22* (2006.01)
*G01N 29/36* (2006.01)

(52) U.S. Cl.
CPC ....... *G01N 29/2418* (2013.01); *G01N 29/222* (2013.01); *G01N 29/2425* (2013.01); *G01N 29/36* (2013.01); *G01N 2291/021* (2013.01)

(58) Field of Classification Search
CPC ............. G01N 29/2418; G01N 29/222; G01N 29/2425; G01N 29/36; G01N 2291/021
USPC ....................................................... 73/24.02
See application file for complete search history.

(56) References Cited

U.S. PATENT DOCUMENTS

| | | | | |
|---|---|---|---|---|
| 5,616,826 A | * | 4/1997 | Pellaux | G01N 21/1702 250/343 |
| 5,753,797 A | * | 5/1998 | Forster | G01N 21/1702 250/343 |
| 6,432,721 B1 | * | 8/2002 | Zook | G01N 1/24 422/82 |
| 6,889,567 B2 | * | 5/2005 | Cabuz | F04B 43/043 417/413.1 |
| 7,398,672 B2 | * | 7/2008 | Riddle | G01N 21/1702 73/24.02 |
| 7,958,771 B2 | * | 6/2011 | Rezachek | G01N 21/1702 73/24.02 |
| 8,983,097 B2 | | 3/2015 | Dehe et al. | |
| 2002/0178782 A1 | * | 12/2002 | Lange | G01N 21/1702 73/23.2 |
| 2002/0194897 A1 | * | 12/2002 | Arnott | G01N 21/1702 73/23.31 |
| 2014/0026639 A1 | * | 1/2014 | Wang | G01N 21/3504 73/24.02 |
| 2017/0350810 A1 | | 12/2017 | Tumpold et al. | |

* cited by examiner

*Primary Examiner* — Son T Le
*Assistant Examiner* — Marrit Eyassu
(74) *Attorney, Agent, or Firm* — Viering, Jentschura & Partner MBB (57) ABSTRACT

A photoacoustic gas detector may include: a gas chamber configured to receive a gas to be analyzed therein, an excitation element configured to selectively excite gas molecules of a specific type that is to be detected in the gas received in the gas chamber in a time-varying fashion, thereby generating pressure differences, a sensor configured to detect pressure differences generated by the excitation element, and a pump configured to pump gas between the exterior of the photoacoustic gas detector and the gas chamber.

23 Claims, 4 Drawing Sheets

# PHOTOACOUSTIC GAS DETECTOR

TECHNICAL FIELD

Various embodiments relate generally to a photoacoustic gas detector, and to a method of operating a photoacoustic gas detector.

BACKGROUND

Photoacoustic gas detectors provide a simple way of analyzing the composition of gases. Since the analysis of the composition of ambient air is becoming increasingly important, e.g., due to pollution, a photoacoustic gas detector that is configured to monitor the concentration of the constituents of a gas with a rapidly changing composition is desirable.

SUMMARY

According to various embodiments, a photoacoustic gas detector is provided. The photoacoustic gas detector may include: a gas chamber configured to receive a gas to be analyzed therein, an excitation element configured to selectively excite gas molecules of a specific type that is to be detected in the gas received in the gas chamber in a time-varying fashion, thereby generating pressure differences such as acoustic waves, a sensor configured to detect pressure differences generated by the excitation element, and a pump configured to pump gas between the exterior of the photoacoustic gas detector and the gas chamber.

According to various embodiments, a method of operating a photoacoustic gas detector is provided. The method may include: operating the photoacoustic gas detector in a sensing mode in which the sensor is read out to determine characteristics of pressure differences to be detected, and operating the photoacoustic gas detector in a pumping mode in which the pump is operated to pump gas between the gas chamber and the exterior of the photoacoustic gas detector.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

Figure 1:
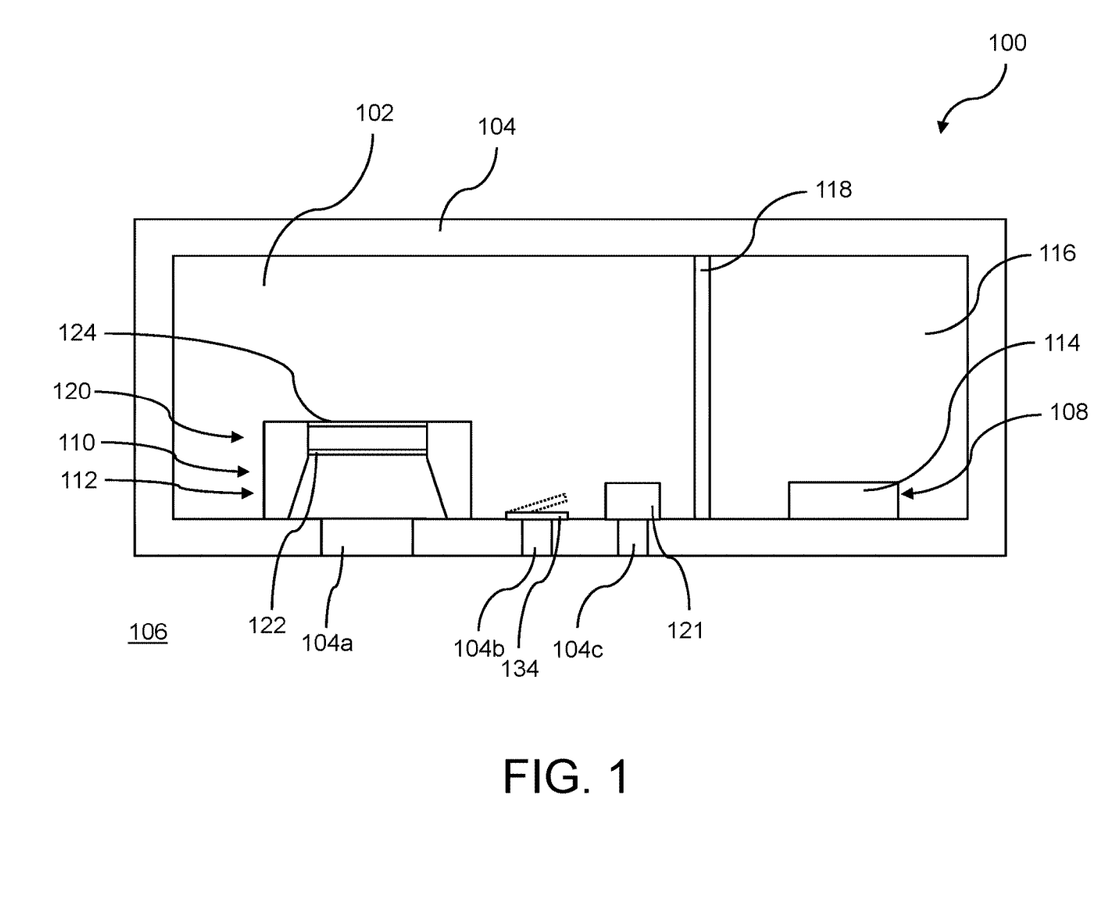
FIG. 1 shows a schematic view of a photoacoustic gas detector.

FIG. 1 shows a schematic view of a photoacoustic gas detector 100. The photoacoustic gas detector 100 may include a gas chamber 102 configured to receive a gas to be analyzed therein. The gas chamber 102 may be delimited by a gas chamber wall 104. The gas chamber wall 104 may include a plurality of through holes 104a, 104b, 104c formed therein and respectively providing gas passages between the exterior 106 of the photoacoustic gas detector 100 and the gas chamber 102.

The photoacoustic gas detector 100 may further include an excitation element 108 (e.g., an optical excitation element) configured to selectively excite gas molecules of a specific type that is to be detected in the gas received in the gas chamber 102 in a time-varying fashion, thereby generating pressure differences such as acoustic waves, a sensor 110 configured to detect pressure differences generated by the excitation element 108, and a pump 112 configured to pump gas between the exterior 106 of the photoacoustic gas detector 100 and the gas chamber 102.

The excitation element 108 may be configured to selectively excite gas molecules of a specific type that is to be detected in the gas received in the gas chamber 102 in a time-varying fashion. The excitation element 108 may be configured to induce a specific atomic or molecular transition in gas molecules of the type that is to be detected and/or to excite various vibrational and/or rotational modes of said gas molecules. During the subsequent de-excitation of the thus excited molecules, heat is generated leading to a local expansion of the gas causing a positive pressure pulse.

The excessive heat generated in this way is subsequently dissipated to a heat sink leading to a contraction of the gas causing a negative pressure pulse. A heat sink may be provided by a holder that is in physical contact with the photoacoustic gas detector 100. The thermal modulation depth (thermal modulation amplitude) may be influenced by means of the thermal coupling to the heat sink or the heat capacity of the heat sink.

Since the gas molecules of the type that is to be detected are excited in a time-varying fashion, e.g., periodically, a time-varying, e.g., periodic, pressure fluctuation is generated in the gas, i.e. acoustic waves that can be detected by the sensor 110.

The photoacoustic gas detector 100 may be used for monitoring the composition of ambient air, e.g., for determining the content of $CO_2$ and/or of toxic gases such as of CO in ambient air. The humidity of ambient air may also be determined in this way. Alternatively or additionally, the photoacoustic gas detector 100 may be configured and used as a breath analyzer to measure the content of alcohol and/or acetone which is indicative of the blood glucose level.

The excitation element 108 may be configured as or may include a radiation source 114 configured to emit electromagnetic radiation adapted to selectively excite gas molecules of a specific type that is to be detected in the gas received in the gas chamber 102 in a time-varying fashion. The radiation source 114 may be configured to emit electromagnetic radiation in the infrared and/or visible and/or ultraviolet frequency range. Infrared light is suitable for exciting vibrational molecular modes. By way of example, infrared light with a wavelength ranging from about 4.170 to about 4.370 μm or from about 14 μm to about 16 μm is suitable for exciting vibrational modes of a $CO_2$ molecule.

The radiation source 114 may be configured as or may include a black-body radiator and/or a laser and/or a photodiode. A black-body radiator is configured to emit electromagnetic radiation according to Planck's law, meaning that its emission spectrum is determined by its temperature but not by its shape or composition. A radiation source 114 configured as or including a black-body radiator may be configured as an electrically heatable body such as a membrane. In operation, the heatable body may be electrically heated up to temperatures higher than 450° C.

The radiation source 114 may be positioned inside of an excitation chamber 116 separated from the gas chamber 102 by means of a window 118 configured to transmit radiation emitted by the radiation source 114. The excitation chamber 116 may be gas tightly sealed from the gas chamber 102 and may be filled with an inert gas such as nitrogen and/or a noble gas. By means of the inert gas, the oxidation of a radiation source 114 configured as or including an electrically heatable black-body radiator may be inhibited.

The window 118 may be configured as or may include a filter configured to selectively transmit electromagnetic radiation emitted by the radiation source 114. In this way, the emission spectrum of the radiation source 114 may be limited to a narrow energy band in order to avoid an unintentional excitation of molecules of other types that are not to be detected in the gas to be analyzed. In this way, the measurement selectivity can be improved as compared to a photoacoustic gas detector that does not include a filter. The filter may be configured as or may include a plasmonic filter and/or a Bragg based laminar filter and/or a Fabry-Pérot interferometer such as a Fabry-Pérot etalon.

The gas chamber 102 may be in permanent gas flow communication with the exterior 106 of the photoacoustic gas detector 100 by means of one of the through holes 104a, 104b, 104c formed in the gas chamber wall 104. In this way, gas can continuously flow between the exterior 106 of the photoacoustic gas detector 100 and the gas chamber 102 by diffusion so that the composition of, e.g., ambient air can be continuously monitored. The diffusion time is mainly determined by the flow areas of the respective gas passages and can range from few seconds to several minutes. Consequently, the concentration of molecules of a certain type may not be accurately determined in case the composition of a gas outside of the photoacoustic gas detector 100 rapidly changes, i.e. on a time scale shorter than the diffusion time.

The gas exchange rate between the exterior 106 of the photoacoustic gas detector 100 and the gas chamber 102 can be increased by actively pumping gas between the exterior 106 of the photoacoustic gas detector 100 and the gas chamber 102 by means of the pump 112.

In the exemplary embodiment shown in FIG. 1, the sensor 110 and the pump 112 are configured as a sensing-pumping unit 120 operable in a sensing mode and in a pumping mode. In the sensing mode, the sensing-pumping unit 120 is configured to detect pressure differences such as acoustic waves generated in the gas received in the gas chamber 102 by the excitation element 108. In the pumping mode, the sensing-pumping unit 120 is configured to pump gas between the exterior 106 of the photoacoustic gas detector 100 and the gas chamber 102. By the provision of the sensing-pumping unit 120 configured to detect pressure differences and to pump gas between the exterior 106 of the photoacoustic gas detector 100 and the gas chamber 102, a photoacoustic gas detector 100 with a compact structure is provided.

It shall not be excluded that additional pumping means separate from the sensing-pumping unit 120 can be provided that are also configured to pump gas between the exterior 106 of the photoacoustic gas detector 100 and the gas chamber 102. An exemplary pumping means 121 that is separately formed from the sensing-pumping unit 120 is shown in FIG. 1. The pumping means 121 is provided adjacently to a through hole 104c provided in the gas chamber wall 104 to pump gas through said through hole 104c between the exterior 106 of the photoacoustic gas detector 100 and the gas chamber 102.

The photoacoustic gas detector 100 may be operated in the sensing mode during a sensing period and may be operated in the pumping mode during a pumping period different from the sensing period. In operation, the photoacoustic gas detector 100 may be repeatedly switched between the two modes. In the pumping mode, the pumping means 121 may be operated simultaneously with the pump 112 to increase the gas exchange rate between the exterior 106 of the photoacoustic gas detector 100 and the gas chamber 102.

As shown in FIG. 1, the sensing-pumping unit 120 may be positioned in an overlapping relationship with a through hole 104a formed in the gas chamber wall 104. In this way, gas can be more efficiently pumped between the exterior 106 of the photoacoustic gas detector 100 and the gas chamber 102. In addition, the sensing-pumping unit 120 may also be employed as a microphone configured to detect acoustic waves generated outside of the photoacoustic gas detector 100. Consequently, the photoacoustic gas detector 100 may be employed in a voice transmission device such as a mobile phone.

Figure 2:
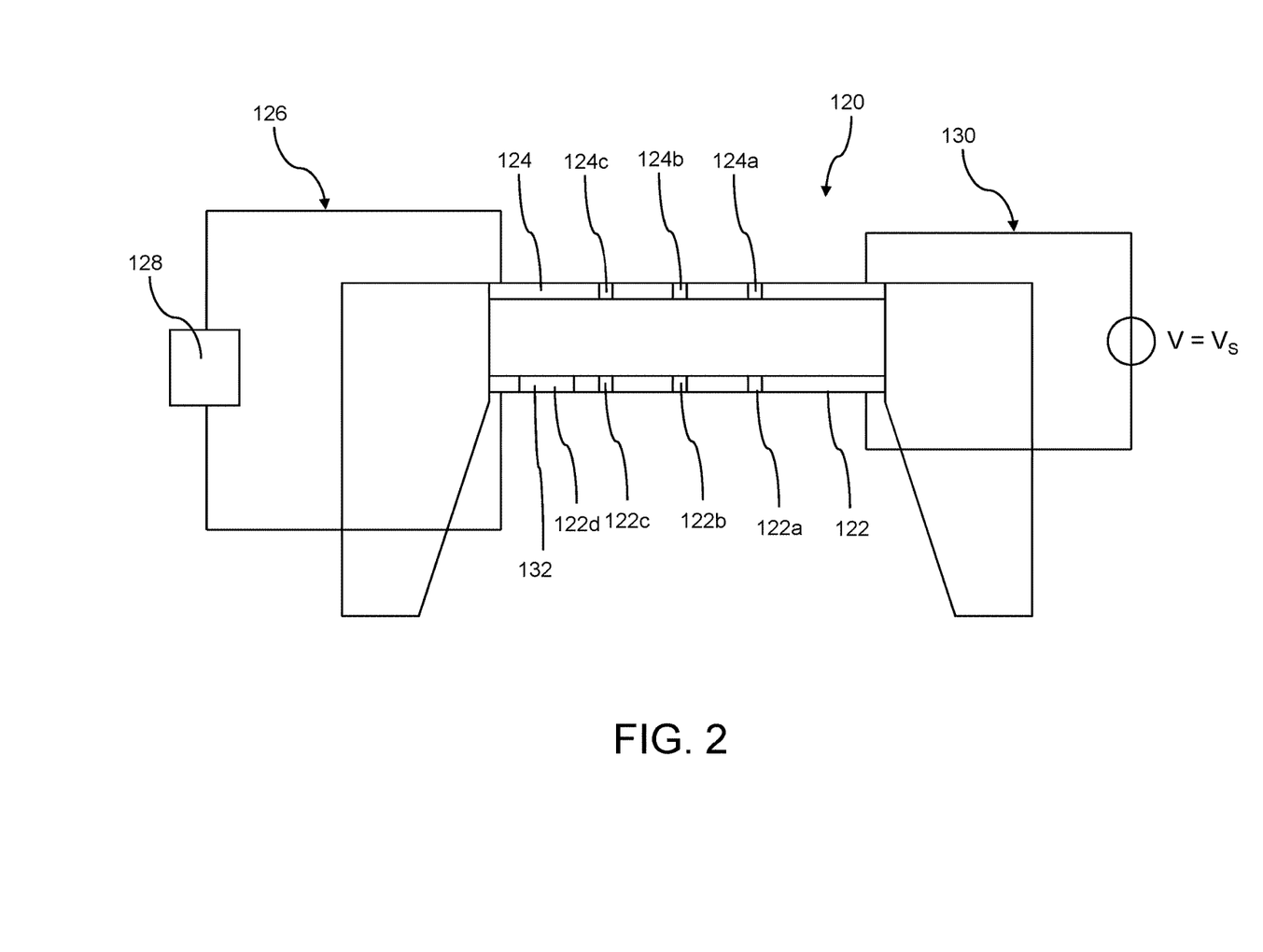
FIG. 2 shows a schematic view of a sensing-pumping unit of the photoacoustic gas detector shown in FIG. 1 in the sensing mode.
Figure 3:
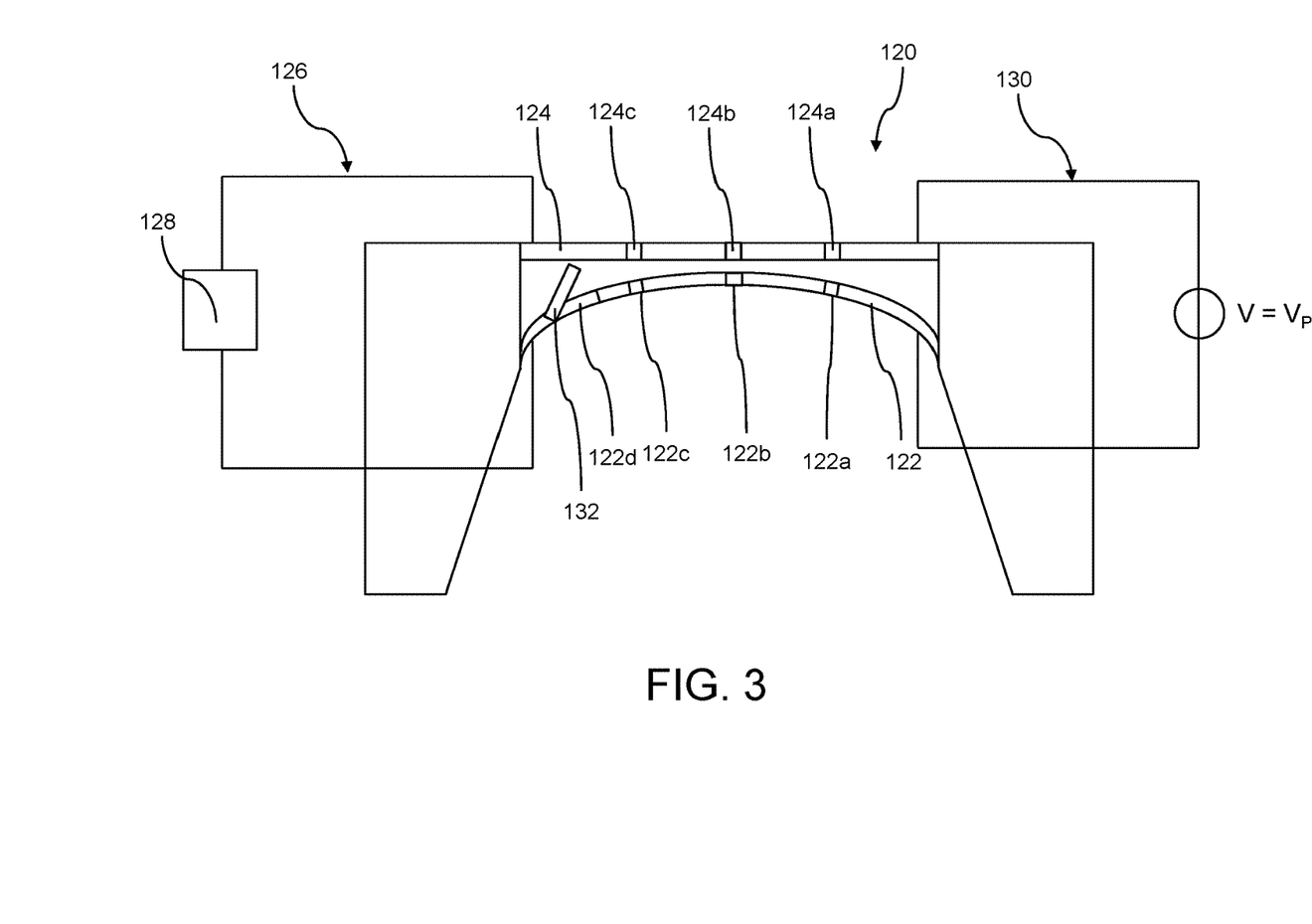
FIG. 3 shows a schematic view of the sensing-pumping unit shown in FIG. 2 in the pumping mode.

As indicated in FIG. 1 and as shown in more detail in FIGS. 2 and 3, the sensing-pumping unit 120 may include a displaceable membrane 122 displaceable by pressure differences such as acoustic waves to be detected in the sensing mode and actively displaceable in the pumping mode to pump gas between the exterior 106 of the photoacoustic gas detector 100 and the gas chamber 102.

The sensing-pumping unit 120 may further include a fixed membrane 124 that is substantially not displaceable in operation. Each of the membranes 122, 124 may be formed at least in part of an electrically conductive material such as of a metal. The displaceable membrane 122 and the fixed membrane 124 may define a capacitor the capacitance of which is alterable by a displacement of the displaceable membrane 122 relative to the fixed membrane 124 caused by acoustic waves to be detected. As indicated in FIG. 2, the capacitance of the capacitor formed by the displaceable membrane 122 and the fixed membrane 124 may be read out in the sensing mode by a read-out circuit 126. The read-out circuit 126 may be integrated into the photoacoustic gas detector 100 and may include a processing unit 128 configured to determine the capacitance of the capacitor and/or to determine therefrom characteristics of the acoustic waves to be detected such as the acoustic pressure and/or the acoustic frequency. The processing unit 128 may include or may be configured as an application specific integrated circuit (ASIC).

The displaceable membrane 122 and the fixed membrane 124 may be electrically connected to a power source 130 configured to apply an electric voltage V to the membranes 122, 124. In the sensing mode, a defined fixed sensing voltage $V_S$ is applied to the membranes 122, 124 by the power source 130. The sensing voltage $V_S$ is lower than an electric voltage required for a full stroke of the displaceable membrane 122, i.e. for bringing the displaceable membrane 122 into physical contact with the fixed membrane 124. The electric voltage required for a full stroke of the displaceable membrane 122 will be referred to in the following as a pull-in voltage $V_{PullIn}$. Hence, in the sensing mode, the sensing voltage $V_S$ applied to the membranes 122, 124 is lower than the pull-in voltage ($V_S<V_{PullIn}$).

As indicated in FIG. 3, in the pumping mode, an electric pumping voltage $V_P$ is applied to the displaceable membrane 122 and to the fixed membrane 124 by the power source 130. This causes a displacement of the displaceable membrane 122 relative to the mechanically fixed membrane 124. The pumping voltage $V_P$ may also be lower than the pull-in voltage $V_{PullIn}$. Since, however, the pumping efficiency depends to a large extent on the stroke of the displaceable membrane 122, the pumping voltage $V_P$ may be larger than the pull-in voltage $V_{PullIn}$, meaning that the membranes 122, 124 are brought into mutual physical contact with each other by means of the electrostatic force generated by the applied pumping voltage $V_P$.

In the exemplary embodiment shown in FIG. 3, the displaceable membrane 122 is displaced towards the fixed membrane 124. In this way, the gas within the gas chamber 102 is temporarily set under pressure which in turn causes the gas to flow out of the gas chamber 102. Subsequently, the electric pumping voltage $V_P$ applied to the membranes 122, 124 may be reduced which in turn reduces the attractive electrostatic force between the membranes 122, 124 causing the distance therebetween to increase, e.g., due to the resiliency of the displaceable membrane 122 biasing the displaceable membrane 122 towards its neutral idle position in which no electrostatic force is exerted onto the membranes 122, 124. This causes the gas pressure inside of the gas chamber 102 to decrease relative to the exterior gas pressure causing gas from the exterior 106 of the photoacoustic gas detector 100 to flow into the gas chamber 102. The above-described cycle of increasing and reducing the electric pumping voltage $V_P$ applied to the membranes 122, 124 may be repeated several times in the pumping mode to provide an efficient gas exchange between the exterior 106 of the photoacoustic gas detector 100 and the gas chamber 102. Consequently, in the pumping mode, the electric voltage applied to the membranes 122, 124 may be larger than the sensing voltage $V_S$. In addition, in contrast to the sensing voltage $V_S$, the pumping voltage $V_P$ is not fixed, but time-varying.

In FIG. 3, the electrostatic force generated between the membranes 122, 124 by the electric pumping voltage $V_P$ is attractive. Alternatively, a repulsive force may be generated between the membranes 122, 124 by applying electric voltages with the same polarities thereto. In this way, the gas pressure in the gas chamber 102 is decreased by a displacement of the displaceable membrane 122 relative to the fixed membrane 124 causing gas from the exterior 106 of the photoacoustic gas detector 100 to flow into the gas chamber 102 as long as there is a pressure gradient between the gas chamber 102 and the exterior 106 of the photoacoustic gas detector 100. As soon as the electric voltages applied to the membranes 122, 124 are reduced, the displaceable membrane 124 returns to its idle position, thereby increasing the gas pressure inside of the gas chamber 102 leading to a gas flow out of the gas chamber 102. The above-described cycle of increasing and reducing the electric voltages applied to the membranes 122, 124 may be repeated several times in the pumping mode to provide an efficient gas exchange between the exterior 106 of the photoacoustic gas detector 100 and the gas chamber 102.

As shown in FIGS. 2 and 3, both the displaceable membrane 122 and the fixed membrane 124 can be provided with through holes 122a, 122b, 122c and 124a, 124b, 124c serving as gas passages. The fixed membrane 124 may include significantly more through holes as compared to the displaceable membrane 122. In this way, the fixed membrane 124 may be made substantially acoustically transparent such that it is substantially not displaceable by acoustic waves to be detected. These through holes may be permanently open. At least one of the membranes 122, 124, e.g., the displaceable membrane 122 can further include a through hole 122d equipped with a gas valve 132 configured to vary the flow area of the through hole 122d. Additionally or alternatively, a through hole 104b provided in the gas chamber wall 104 can be equipped with a gas valve 134 configured to vary the gas flow area of the respective through hole 104b. As indicated in FIG. 1, the gas valve 134 may be configured to completely close the through hole 104b (position of the gas valve 134 drawn by the solid line). The gas valve 134 in an open position is drawn in FIG. 1 by a dotted line.

The gas valves 132, 134 may be operated such as to close the respective through holes 122d, 104b in a state in which there is substantially no difference between the gas pressure in the gas chamber 102 and the exterior 106 of the photoacoustic gas detector 100, and to open the respective through holes 122d, 104b in a state in which there is a substantial difference between the gas pressure in the gas chamber 102 and outside of the photoacoustic gas detector 100. In this way, the gas flow area between the exterior 106 of the photoacoustic gas detector 100 and the gas chamber 102 can be increased, thereby enabling a faster gas exchange between the exterior 106 of the photoacoustic gas detector 100 and the gas chamber 102.

As shown in FIG. 1, the sensing-pumping unit 120, i.e. the displaceable membrane 122 and the fixed membrane 124 may be positioned inside of the gas chamber 102. In this way, a photoacoustic gas detector 100 with a compact structure may be provided.

In a modified embodiment, the photoacoustic gas detector 100 may be provided with heating means configured to heat the gas inside of the gas chamber 102 in a time-varying fashion in the pumping mode. In this way, the gas pressure inside of the gas chamber 102 can be increased relative to the gas pressure outside of the photoacoustic gas detector 100 in order to pump gas between the exterior 106 of the photoacoustic gas detector 100 and the gas chamber 102.

Figure 4:
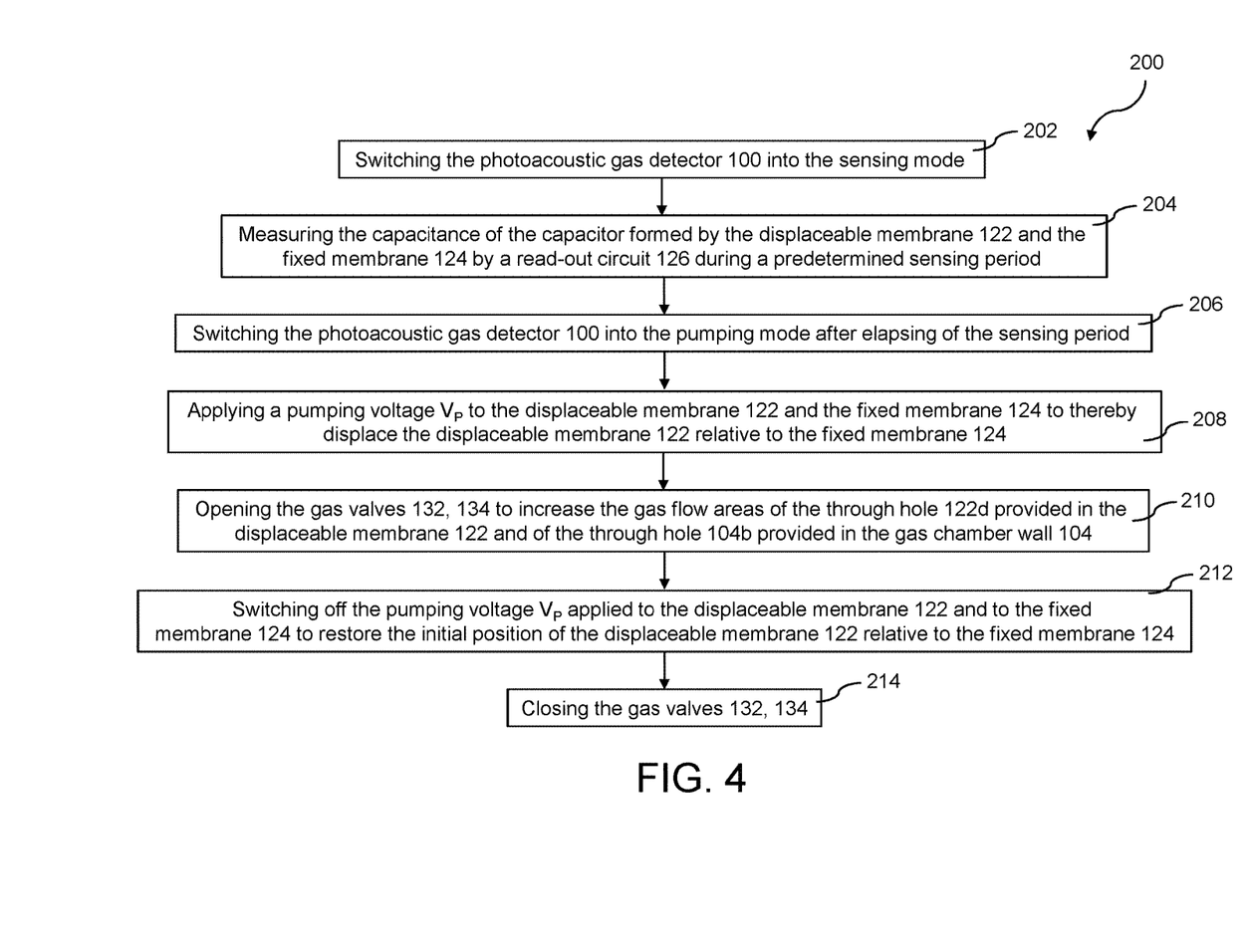
FIG. 4 shows a flow diagram of an exemplary method of operating the photoacoustic gas detector shown in FIGS. 1 to 3.

A flow diagram of an exemplary method 200 of operating the photoacoustic gas detector 100 shown in FIG. 1 is depicted in FIG. 4. The method 200 may include:

Switching the photoacoustic gas detector 100 into the sensing mode (202);

Measuring the capacitance of the capacitor formed by the displaceable membrane 122 and the fixed membrane 124 by a read-out circuit 126 during a predetermined sensing period (204);

Switching the photoacoustic gas detector 100 into the pumping mode after elapsing of the sensing period (206);

Applying a pumping voltage $V_P$ to the displaceable membrane 122 and the fixed membrane 124 to thereby displace the displaceable membrane 122 relative to the fixed membrane 124 (208);

Opening the gas valves 132, 134 to increase the gas flow areas of the through hole 122d provided in the displaceable membrane 122 and of the through hole 104b provided in the gas chamber wall 104 (210);

Switching off the pumping voltage $V_P$ applied to the displaceable membrane 122 and to the fixed membrane 124 to restore the idle position of the displaceable membrane 122 relative to the fixed membrane 124 (212); and Closing the gas valves 132, 134 (214).

In the above exemplary method of operating the photoacoustic gas detector 100, only one pumping cycle is described. This pumping cycle may of course be repeated a plurality of times during the pumping period to provide an efficient gas exchange between the gas chamber 102 and the exterior 106 of the photoacoustic gas detector 100. The repetition rate of the pumping cycles as well as the pumping cycle itself can be varied based on the pressure in the photoacoustic gas detector 100 and the pressure outside thereof.

In a modified embodiment, the sensing-pumping unit 120 may include a piezoelectric member provided on the displaceable membrane 122. The piezoelectric member may be configured to generate an electric voltage in the sensing mode as a result of a displacement of the displaceable membrane 122 induced by acoustic waves. The thus generated electric voltage may be indicative of characteristics of the acoustic waves. By applying an electric voltage to the piezoelectric member, the displaceable membrane 122 may be displaced to pump gas between the exterior 106 of the photoacoustic gas detector 100 and the gas chamber 102 in the pumping mode.

In yet another modified embodiment, the sensing-pumping unit 120 may include a fixed first electromagnetic interaction member and a displaceable second electromagnetic interaction member mounted on the displaceable membrane 122. In the sensing mode, one of the first and second electromagnetic interaction members may be configured to induce an electric voltage in the respective other one of the first and second electromagnetic interaction members by a displacement of the displaceable membrane 122. The first and second electromagnetic interaction members may be configured to individually generate a magnetic field to actively displace the displaceable membrane 122 to pump gas between the exterior 106 of the photoacoustic gas detector 100 and the gas chamber 102 in the pumping mode.

The first and second electromagnetic interaction members may be configured as or may include respective coils. In this way, in the sensing mode one of the coils may be operated as an electric magnet that is configured to induce an electric voltage in the respective other coil by means of the displacement of the displaceable membrane 122 induced by acoustic waves to be detected. The thus induced electric voltage may be indicative of characteristics of the acoustic waves to be detected. In the pumping mode, both coils may be operated as electric magnets to generate respective magnetic fields by means of which an attractive or repulsive force may be generated between the membranes 122, 124 to pump gas between the gas chamber 102 and the exterior 106 of the photoacoustic gas detector 100.

Alternatively, one of the first and second electromagnetic interaction members may be configured as a permanent magnet and the respective other one may include a coil in which an electric voltage may be induced by the permanent magnet in the above-described way in the sensing mode. In the pumping mode, the coil may be operated as an electric magnet to generate a magnetic field that interacts with the magnetic field generated by the permanent magnet to actively displace the displaceable membrane 122 to pump gas between the gas chamber 102 and the exterior 106 of the photoacoustic gas detector 100.

In the following, various aspects of this disclosure will be illustrated:

Example 1 is a photoacoustic gas detector. The photoacoustic gas detector may include: a gas chamber configured to receive a gas to be analyzed therein, an excitation element configured to selectively excite gas molecules of a specific type that is to be detected in the gas received in the gas chamber in a time-varying fashion, thereby generating pressure differences such as acoustic waves, a sensor configured to detect pressure differences such as acoustic waves generated by the excitation element, and a pump configured to pump gas between the exterior of the photoacoustic gas detector and the gas chamber.

In Example 2, the subject matter of Example 1 can optionally further include that the sensor and the pump are configured as a sensing-pumping unit operable in a sensing mode and in a pumping mode. The sensing-pumping unit may be configured to detect pressure differences generated by the excitation element in the sensing mode, and to pump gas between the exterior of the photoacoustic gas detector and the gas chamber in the pumping mode.

In Example 3, the subject matter of Example 2 can optionally further include that the sensing-pumping unit includes a displaceable membrane displaceable by pressure differences to be detected in the sensing mode and actively displaceable to pump gas between the exterior of the photoacoustic gas detector and the gas chamber in the pumping mode.

In Example 4, the subject matter of Example 3 can optionally further include that the displaceable membrane includes at least one through hole formed therethrough providing a gas passage.

In Example 5, the subject matter of Example 4 can optionally further include that the displaceable membrane is equipped with a gas valve configured to vary the gas flow area of at least one through hole formed in the displaceable membrane.

In Example 6, the subject matter of any one of Examples 3 to 5 can optionally further include that the sensing-pumping unit includes a fixed membrane positioned adjacently to the displaceable membrane. The photoacoustic gas detector may further include: a read-out circuit configured to measure the capacitance between the displaceable and fixed membranes in the sensing mode, the capacitance being changeable by a displacement of the displaceable membrane relative to the fixed membrane caused by acoustic waves, and a change in the capacitance being indicative of characteristics of the acoustic waves to be detected, and a power source configured to apply an electric voltage to the displaceable and fixed membranes in the pumping mode to generate an electrostatic force between the membranes to displace the displaceable membrane relative to the fixed membrane to generate a pumping force.

In Example 7, the subject matter of Example 6 can optionally further include that the fixed membrane includes at least one through hole formed therethrough providing a gas passage.

In Example 8, the subject matter of Example 7 can optionally further include that the fixed membrane is equipped with at least one gas valve configured to vary the gas flow area of at least one through hole formed in the fixed membrane.

In Example 9, the subject matter of any one Examples 1 to 8 can optionally further include that the gas chamber is delimited by a gas chamber wall including at least one through hole formed therethrough, the through hole providing a gas passage between the gas chamber and the exterior of the photoacoustic gas detector.

In Example 10, the subject matter of Example 9 can optionally further include that the gas chamber wall is equipped with at least one gas valve configured to vary the gas flow area of at least one through hole formed in the gas chamber wall.

In Example 11, the subject matter of any one of Examples 9 or 10 and of any one of Examples 2 to 8 can optionally further include pumping means different from the sensing-pumping unit. The pumping means may be configured to pump gas between the exterior of the photoacoustic gas detector and the gas chamber through at least one through hole formed in the gas chamber wall.

In Example 12, the subject matter of any one of Examples 9 to 11 and of any one of Examples 3 to 8 can optionally further include that the displaceable membrane and a through hole formed in the gas chamber wall mutually overlap.

In Example 13, the subject matter of any one of Examples 3 to 12 can optionally further include that the displaceable membrane is positioned inside of the gas chamber.

In Example 14, the subject matter of any one of Examples 6 to 13 can optionally further include that the fixed membrane is positioned inside of the gas chamber.

In Example 15, the subject matter of any one of Examples 1 to 14 can optionally further include heating means configured to heat the gas in the gas chamber in a time-varying fashion.

In Example 16, the subject matter of any one of Examples 1 to 15 can optionally further include that the excitation element is configured as or includes a radiation source configured to emit electromagnetic radiation configured to selectively excite gas molecules of a specific type that is to be detected in the gas received in the gas chamber in a time-varying fashion, thereby generating acoustic waves.

In Example 17, the subject matter of Example 16 can optionally further include that the radiation source is configured to emit electromagnetic radiation in the infrared and/or visible and/or ultraviolet frequency range.

In Example 18, the subject matter of any one of Examples 1 to 17 can optionally further include that the excitation element is positioned inside of the gas chamber or in an excitation chamber separated from the gas chamber.

In Example 19, the subject matter of Example 18 and of any one of Examples 16 or 17 can optionally further include that the excitation chamber is separated from the gas chamber by a window configured to transmit electromagnetic radiation emitted by the radiation source.

In Example 20, the subject matter of Example 19 can optionally further include that the window includes or is configured as a filter configured to selectively transmit electromagnetic radiation emitted by the radiation source.

In Example 21, the subject matter of Examples 20 can optionally further include that the filter includes or is configured as a plasmonic filter and/or a Bragg mirror and/or a Fabry-Pérot interferometer such as a Fabry-Pérot etalon.

Example 22 is a mobile device including a photoacoustic gas detector of any one of Examples 1 to 21.

In Example 23, the mobile device of Example 22 can be optionally configured as a mobile phone.

Example 24 is a method of operating a photoacoustic gas detector of any one of Examples 1 to 21. The method may include: operating the photoacoustic gas detector in a sensing mode in which the sensor is read out to determine characteristics of acoustic waves to be detected, and operating the photoacoustic gas detector in a pumping mode in which the pump is operated to pump gas between the gas chamber and the exterior of the photoacoustic gas detector.

In Example 25, the subject matter of Example 24 can optionally further include that the photoacoustic gas detector is operated in the sensing mode during a sensing period and is operated in the pumping mode during a pumping period different from the sensing period.

In Example 26, the subject matter of any one of Examples 24 or 25 can optionally further include that the sensor and the pump are configured as a sensing-pumping unit including a displaceable membrane. In the sensing mode a displacement of the displaceable membrane caused by acoustic waves may be sensed, and in the pumping mode the displaceable membrane may be actively displaced to pump gas between the exterior of the photoacoustic gas detector and the gas chamber.

In Example 27, the subject matter of Example 26 can optionally further include that the sensing-pumping unit further includes a fixed membrane defining a capacitor with the displaceable membrane the capacitance of which is alterable by a displacement of the displaceable membrane. The method may further include: measuring the capacitance of the capacitor in the sensing mode, and applying a time-varying electric voltage to the displaceable and the fixed membrane to actively displace the displaceable membrane relative to the fixed membrane to pump gas between the exterior of the photoacoustic gas detector and the gas chamber.

In Example 28, the subject matter of any one of Examples 24 to 27 can optionally further include that the photoacoustic gas detector further includes a gas passage between the exterior of the photoacoustic gas detector and the gas chamber. The gas passage may be equipped with a gas valve configured to vary the gas flow area and/or flow impedance of the gas passage. The method may further include varying the gas flow area and/or flow impedance of the gas passage by means of the gas valve in the pumping mode.

In Example 29, the subject matter of any one of Examples 24 to 28 can optionally further include that the photoacoustic gas detector includes heating means configured to heat the gas in the gas chamber in a time-varying fashion. The method may further include: heating the gas in the gas chamber in the pumping mode in a time-varying fashion.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A photoacoustic gas detector, comprising:
a gas chamber configured to receive a gas to be analyzed therein;
an excitation element configured to selectively excite gas molecules of a specific type that is to be detected in the gas received in the gas chamber in a time-varying fashion, thereby generating acoustic waves;
a sensor configured to detect acoustic waves generated by the excitation element; and
a pump configured to pump gas between the exterior of the photoacoustic gas detector and the gas chamber,
wherein the sensor and the pump are configured as a sensing-pumping unit operable in a sensing mode and in a pumping mode, wherein the sensing-pumping unit is configured to detect acoustic waves generated by the excitation element in the sensing mode, and to pump gas between the exterior of the photoacoustic gas detector and the gas chamber in the pumping mode,
wherein the sensing-pumping unit comprises a displaceable membrane displaceable by acoustic waves to be detected in the sensing mode and actively displaceable to pump gas between the exterior of the photoacoustic gas detector and the gas chamber in the pumping mode, and wherein the displaceable membrane comprises at least one through hole formed therethrough providing a gas passage.

2. The photoacoustic gas detector of claim 1,
wherein the displaceable membrane is equipped with a gas valve configured to vary the gas flow area and/or flow impedance of one of the at least one through hole formed in the displaceable membrane.

3. The photoacoustic gas detector of claim 1,
wherein the sensing-pumping unit further comprises a fixed membrane positioned adjacently to the displaceable membrane,
wherein the photoacoustic gas detector further comprises:
a read-out circuit configured to measure the capacitance between the displaceable and fixed membranes in the sensing mode, wherein the capacitance is changeable by a displacement of the displaceable membrane relative to the fixed membrane caused by acoustic waves, wherein a change in the capacitance is indicative of characteristics of the acoustic waves to be detected; and
a power source configured to apply an electric voltage to the displaceable and fixed membranes in the pumping mode to generate an electrostatic force between the membranes to displace the displaceable membrane relative to the fixed membrane to generate a pumping force.

4. The photoacoustic gas detector of claim 3,
wherein the fixed membrane comprises at least one through hole formed therethrough providing a gas passage.

5. The photoacoustic gas detector of claim 4,
wherein the fixed membrane is equipped with at least one gas valve configured to vary the gas flow area and/or flow impedance of the at least one through hole formed in the fixed membrane.

6. The photoacoustic gas detector of claim 3,
wherein the fixed membrane is positioned inside of the gas chamber.

7. The photoacoustic gas detector of claim 1,
wherein the gas chamber is delimited by a gas chamber wall comprising at least one through hole formed therethrough, wherein the at least one through hole formed in the gas chamber wall provides a gas passage between the gas chamber and the exterior of the photoacoustic gas detector.

8. The photoacoustic gas detector of claim 7,
wherein the gas chamber wall is equipped with at least one gas valve configured to vary the gas flow area and/or flow impedance of the at least one through hole formed in the gas chamber wall.

9. The photoacoustic gas detector of claim 7,
wherein the sensing-pumping unit is disposed to align or overlap with the at least one through hole formed in the gas chamber wall.

10. The photoacoustic gas detector of claim 7,
wherein the gas chamber is in permanent gas flow communication with the exterior of the photoacoustic gas detector via the at least one through hole formed in the gas chamber wall.

11. The photoacoustic gas detector of claim 1,
wherein the gas chamber is delimited by a gas chamber wall comprising at least one through hole formed therethrough, wherein the photoacoustic gas detector further comprises pumping means different from the sensing-pumping unit, wherein the pumping means are configured to pump gas between the exterior of the photoacoustic gas detector and the gas chamber through the at least one through hole formed in the gas chamber wall.

12. The photoacoustic gas detector of claim 1,
wherein the displaceable membrane is positioned inside of the gas chamber.

13. The photoacoustic gas detector of claim 1, further comprising
heating means configured to heat the gas in the gas chamber in a time-varying fashion.

14. The photoacoustic gas detector of claim 1,
wherein the excitation element is configured as or comprises a radiation source configured to emit electromagnetic radiation configured to selectively excite gas molecules of a specific type that is to be detected in the gas received in the gas chamber in a time-varying fashion, thereby generating acoustic waves.

15. The photoacoustic gas detector of claim 14,
wherein the radiation source is configured to emit electromagnetic radiation in the infrared and/or visible and/or ultraviolet frequency range.

16. The photoacoustic gas detector of claim 1,
wherein the excitation element is positioned inside of the gas chamber or in an excitation chamber separated from the gas chamber.

17. The photoacoustic gas detector of claim 16,
wherein the excitation element is configured as or comprises a radiation source configured to emit electromagnetic radiation configured to selectively excite gas molecules of a specific type that is to be detected in the gas received in the gas chamber in a time-varying fashion, thereby generating acoustic waves, wherein the excitation chamber is separated from the gas chamber by a window configured to transmit electromagnetic radiation emitted by the radiation source.

18. The photoacoustic gas detector of claim 17, wherein the window comprises or is configured as a filter configured to selectively transmit electromagnetic radiation emitted by the radiation source.

19. A method of operating a photoacoustic gas detector, wherein the photoacoustic gas detector comprises:
a gas chamber configured to receive a gas to be analyzed therein;
an excitation element configured to selectively excite gas molecules of a specific type that is to be detected in the gas received in the gas chamber in a time-varying fashion, thereby generating acoustic waves;
a sensor configured to detect acoustic waves generated by the excitation element; and
a pump configured to pump gas between the exterior of the photoacoustic gas detector and the gas chamber,
wherein the sensor and the pump are configured as a sensing-pumping unit operable in a sensing mode and in a pumping mode, wherein the sensing-pumping unit is configured to detect acoustic waves generated by the excitation element in the sensing mode, and to pump gas between the exterior of the photoacoustic gas detector and the gas chamber in the pumping mode,
wherein the sensing-pumping unit comprises a displaceable membrane,
wherein in the sensing mode a displacement of the displaceable membrane caused by acoustic waves is sensed, and in the pumping mode the displaceable membrane is actively displaced to pump gas between the exterior of the photoacoustic gas detector and the gas chamber, and wherein the displaceable membrane comprises at least one through hole formed therethrough providing a gas passage, wherein the method comprises:

operating the photoacoustic gas detector in a sensing mode in which the sensor is read out to determine characteristics of acoustic waves to be detected; and operating the photoacoustic gas detector in a pumping mode in which the pump is operated to pump gas between the gas chamber and the exterior of the photoacoustic gas detector.

20. The method of claim 19, wherein the photoacoustic gas detector is operated in the sensing mode during a sensing period and is operated in the pumping mode during a pumping period different from the sensing period.

21. The method of claim 19, wherein the sensing-pumping unit further comprises a fixed membrane defining a capacitor with the displaceable membrane the capacitance of which is alterable by a displacement of the displaceable membrane, wherein the method further comprises:

measuring the capacitance of the capacitor in the sensing mode; and applying a time-varying electric voltage to the displaceable and the fixed membranes to actively displace the displaceable membrane relative to the fixed membrane to pump gas between the exterior of the photoacoustic gas detector and the gas chamber.

22. The method of claim 19, wherein the photoacoustic gas detector further comprises a gas passage between the exterior of the photoacoustic gas detector and the gas chamber, wherein the gas passage is equipped with a gas valve configured to vary the gas flow area and/or flow impedance of the gas passage, wherein the method further comprises varying the gas flow area and/or flow impedance of the gas passage by means of the gas valve in the pumping mode.

23. The method of claim 19, wherein the photoacoustic gas detector comprises heating means configured to heat the gas in the gas chamber in a time-varying fashion, wherein the method further comprises:

heating the gas in the gas chamber in the pumping mode in a time-varying fashion.

\* \* \* \* \*